US006566142B1

(12) United States Patent
Gateau et al.

(10) Patent No.: US 6,566,142 B1
(45) Date of Patent: May 20, 2003

(54) LABORATORY TEST FOR ASSESSING THE TENDENCY OF A GASOLINE, OPTIONALLY CONTAINING AN ADDITIVE, TO CAUSE DEPOSITS WHILE THE ENGINE IS RUNNING

(75) Inventors: Patrick Gateau, Maurepas (FR); Fabrice Paille, Limay (FR); Yves Boscher, Argenteuil (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/622,664

(22) PCT Filed: Dec. 6, 1999

(86) PCT No.: PCT/FR99/03027

§ 371 (c)(1),
(2), (4) Date: Aug. 22, 2000

(87) PCT Pub. No.: WO00/37936

PCT Pub. Date: Jun. 29, 2000

(30) Foreign Application Priority Data

Dec. 28, 1998  (FR) .............................................. 98/16294

(51) Int. Cl.[7] ................................................ G01N 33/22
(52) U.S. Cl. ...................... 436/139; 73/61.62; 436/155; 436/160; 436/177
(58) Field of Search ................................ 436/139, 177, 436/155, 160; 73/61.62

(56) References Cited

U.S. PATENT DOCUMENTS

| | | | |
|---|---|---|---|
| 3,059,467 A | * | 10/1962 | Megerian et al. |
| 3,108,468 A | * | 10/1963 | Mickel |
| 3,670,561 A | * | 6/1972 | Hundere |
| 5,492,005 A | | 2/1996 | Homan et al. |
| 5,693,874 A | | 12/1997 | De La Cruz et al. |
| 5,967,765 A | * | 10/1999 | Henderson et al. |

FOREIGN PATENT DOCUMENTS

GB        2 281 620        3/1995

OTHER PUBLICATIONS

Derwent WPI Week 9417; SU 1 797 057.

* cited by examiner

*Primary Examiner*—Jan Ludlow
(74) *Attorney, Agent, or Firm*—Millen, White, Zelano & Branigan, P.C.

(57) ABSTRACT

A new laboratory test for evaluating the tendency of a gasoline, which may contain additives, to produce deposits during running of an engine involves the following steps: a tube is placed in the injector oven of a gas chromatograph; said tube is kept at a constant temperature in a constant flow of air; the gasoline or additive-containing gasoline to be evaluated is injected through said tube; and the quantity of deposits formed is determined by weighing said tube after dismantling.

12 Claims, 1 Drawing Sheet

LABORATORY TEST FOR ASSESSING THE TENDENCY OF A GASOLINE, OPTIONALLY CONTAINING AN ADDITIVE, TO CAUSE DEPOSITS WHILE THE ENGINE IS RUNNING

The invention relates to a novel laboratory test for evaluating the tendency of a gasoline, which may contain additives, to produce deposits during running of an engine.

Deposits from fuels and lubricants form in an engine throughout its running. Such deposits are produced by heat in an oxidising medium in the various elements of the feed circuit (carburettor, injectors, inlet valves) and in the combustion chambers (cylinder head, piston crown, exhaust valve, spark plug). They cause running perturbations by degrading conduit tuning, increasing emissions or even destroying the engine.

Numerous additives and additive formulations have been developed to prevent such fouling,. They are generally polymeric surfactants comprising a lipophilic portion which ensures solubility and a polar portion which can be adsorbed on the engine walls to protect them or onto insoluble particles to keep them in suspension. In the case of spark ignition engines, they are also usually associated with a carrier oil which can be a polyolefin or a polyether. Such additives are effective in reducing and even preventing deposits from being formed in the feed circuit but do not reduce the deposits in the combustion chambers. It has also been shown that such additives can cause an increase in such deposits.

The tendency of a gasoline to produce deposits when an engine is running is generally evaluated by bench engine tests but such tests are long, expensive and require unwieldy equipment as well as a large quantity of fuel. Different engine tests have to be carried out to measure fouling in different parts of the engine. The engine test which is most frequently used in Europe to evaluate the ability of a gasoline or an additive-containing gasoline to keep the inlet valves clean is the Mercedes 102E engine test which lasts 60 hours, requiring about 300 liters of fuel.

A number of laboratory tests have been proposed in the past to simulate fouling in the different parts of an engine but until now none have led to sufficiently predictive results to be generally used. In 1997, an investigative group (IF031) charged by the Co-ordination European Council (CEC) to examine laboratory tests which could evaluate the quality of gasoline and diesel fuel as regards deposits concluded that no method existed which could achieve that aim. Only a Honda engine test lasting 20 hours and an analysis based on the thermogravimetry of gums in a gasoline could, in the best of cases, permit pre-selection to be carried out to develop additives.

The present invention proposes a novel laboratory test intended to evaluate the tendency of a gasoline, which may contain additives, to produce deposits on the inlet valves and in the combustion chambers.

The method of the invention can be defined in general in that a tube is placed in the injector oven of a gas chromatograph; said tube is kept at a constant temperature in a constant flow of air; the gasoline or additive-containing gasoline to be evaluated is injected through said tube; and the quantity of deposits formed is determined by weighing said tube after dismantling.

Figure 1:
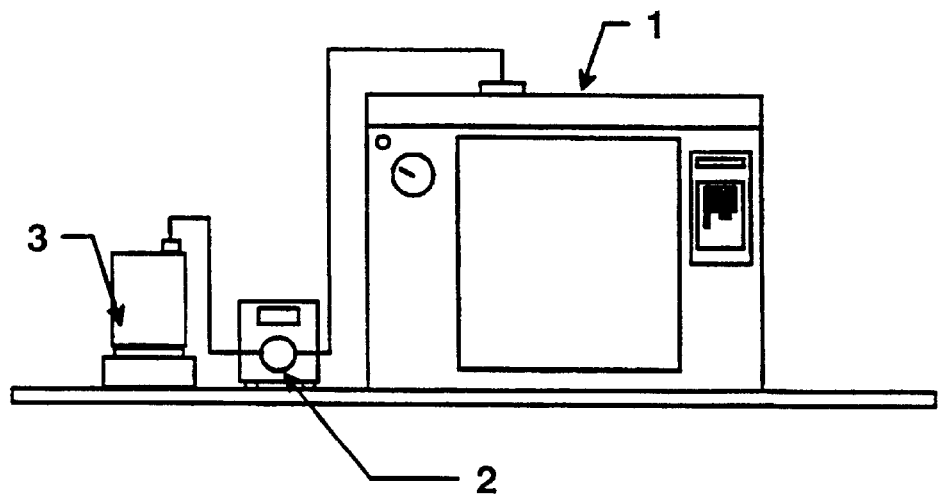
FIG. 1 is a diagrammatic representation of the equipment used to carry out the test of the invention.
Figure 2:
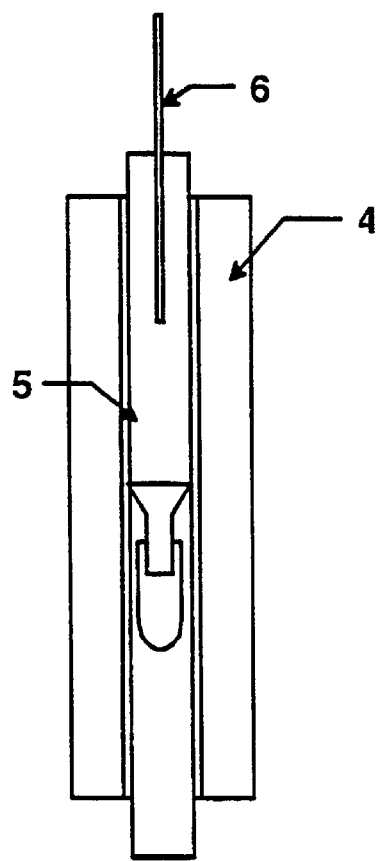
FIG. 2 shows an arrangement of the chromatograph oven tube and a needle which can be used to carry out the test.

The invention will be described in more detail below with reference to FIGS. 1 and 2. The numbers in brackets refer to those in the figures.

More particularly, a tube (5) consists of a gas chromatograph injector (1), for example of glass. This liner can be a straight tube with a diameter and length which is suitable for the injector used (for example internal diameter=4 mm and length=80 mm) or a liner with a mixing chamber such as a cup splitter with reference Hewlett-Packard 18740-80190®. This latter type is selected when the tendency of the fuel to produce deposits is small.

Tube (5) is placed in the injector oven (4). It is kept at a constant temperature in a constant flow of air regulated by the flow meter of chromatograph (1). The gasoline or additive-containing gasoline to be evaluated is injected through tube (5) using a needle (6) usually positioned such that injection is made at a depth of about 10 mm inside the tube (5). The gasoline is injected by means of a pump (2) at a flow rate of 0.5 to 2 kg, preferably of the order of 1 kg per 24 hours. The mass injected is monitored by weighing using a balance (3).

The quantity of deposits formed is determined by weighing tube (5) after dismantling.

In the method of the invention, the importance of temperature on the quantity of deposits formed has been able to be demonstrated and it has been possible to define two temperature ranges in relation to the conditions encountered in an engine. At a temperature in the range 250° C. to 300° C. and preferably at a temperature close to 275° C., the laboratory test of the invention behaves as a representative test for inlet valves, while in the temperature range 325° C. to 375° C. and preferably at 350° C., said test is representative of the combustion chambers.

In a preferred implementation of the invention, prior to injection, the gasoline to be evaluated is freed of 15% to 25% and preferably 20% by weight of its lightest fractions by flushing with an inert gas at ambient temperature. It is generally accepted that only the heavy fractions are responsible for the formation of deposits and such a procedure can prevent degassing of the gasoline at the pump which would cause the pump to de-prime.

The following examples illustrate the invention but are in no way to be considered to be limiting.

EXAMPLE 1

A reference gasoline with the characteristics shown in Table 1 and from which 20% by weight had been eliminated by flushing with argon at ambient temperature was introduced by means of a PROEMINENT® reciprocating pump, in an amount of 1 kg over 24 hours, into a glass liner (HEWLETT-PACKARD 18740-80190®) of a gas phase chromatograph via a needle positioned so that injection was made at a depth of 10 mm into the liner, the temperature of the injector being held at 275° C. At the end of the test, after cooling, the liner was dismantled and weighed. The weight of the deposit obtained was 30.5 mg.

TABLE 1

| | |
|---|---|
| Research octane number | 96.8 |
| Density at 15° C. | 754 kg/m$^3$ |
| Reid vapour pressure | 618 hPa |
| Distillation | |

TABLE 1-continued

| | |
|---|---|
| Initial point | 30.7° C. |
| 5% | 45.0° C. |
| 10% | 51.5° C. |
| 20% | 65.5% |
| 30% | 80.5° C. |
| 40% | 97.0° C. |
| 50% | 111.0° C. |
| 60% | 123.0° C. |
| 70% | 138.0° C. |
| 80% | 154.5° C. |
| 90% | 172.8° C. |
| 95% | 185.0° C. |
| End point | 205.0° C. |

EXAMPLES 2 TO 4

With everything else being equal, different quantities of a commercial detergent additive were added to the gasoline to be evaluated of Example 1, and the results shown in Table 2 were obtained. That table also shows results of Mercedes 102E tests (CEC procedure F-05-A-93) obtained with the same gasoline samples and expressed as the mass of deposits over the 4 inlet valves.

TABLE 2

| | | Weight of deposits (mg) | |
|---|---|---|---|
| Example | Detergent additive (ppm) | Test of invention (T = 275° C.) | M102E engine test |
| 1 | 0 | 30.5 | 1131 |
| 2 | 50 | 46.0 | 1807 |
| 3 | 250 | 27.2 | 652 |
| 4 | 500 | 9.0 | 37 |

These results show that the laboratory test of the invention (T=275° C.) properly produced the effects of a commercial detergent additive on the weight of the deposits on the inlet valves.

EXAMPLES 5 TO 8

Examples 1 to 4 were repeated, the only exception being that the temperature was kept at 350° C. instead of 275° C. The results shown in Table 3 were obtained. That table also shows the weight of deposits collected in the combustion chambers of Mercedes 102E tests (CEC procedure F-05-A-93) produced with the same gasoline samples.

TABLE 3

| | | Weight of deposits (mg) | |
|---|---|---|---|
| Example | Detergent additive (ppm) | Test of invention (T = 350° C.) | M102E engine test |
| 5 | 0 | 14.1 | 5255 |
| 6 | 50 | 15.0 | 6805 |
| 7 | 250 | 21.8 | 8428 |
| 8 | 500 | 60.7 | 11100 |

These results show that the laboratory test of the invention carried out at 350° C. properly reproduced the influence of a commercial detergent additive on the weight of deposits formed in the combustion chambers.

What is claimed is:

1. A laboratory method for evaluating the tendency of a gasoline or an additive-containing gasoline to produce deposits during running of an engine, comprising placing a tube in an oven maintaining said tube at a constant temperature in a constant flow of air;

injecting the gasoline or additive-containing gasoline to be evaluated through said tube;

and determining the quantity of deposits formed by weighing said tube after dismantling;

and wherein prior to said injecting, the gasoline to be evaluated is freed of 15% to 25% by weight of its lightest fractions by flushing with an inert gas.

2. A method according to claim 1, wherein gasoline to be evaluated is freed of 20% by weight of its lightest fractions by flushing with an inert gas.

3. A method according to claim 1, wherein said flushing with an inert gas is conducted at ambient temperature.

4. A method according to claim 1, wherein said tube is glass.

5. A method according to claim 4, wherein the glass tube has a mixing chamber.

6. A method according to claim 1, wherein the gasoline or additive-containing gasoline to be evaluated is injected at a constant flow rate of 0.5 to 2 kg per 24 hours.

7. A method according to claim 1, wherein the gasoline or additive-containing gasoline to be evaluated is injected at a constant flow rate of about 1 kg per 24 hours.

8. A method according to claim 1, adapted to evaluate the tendency of a gasoline or an additive-containing gasoline to produce deposits on inlet valves, and wherein the temperature is kept constant at a value of 250° C. to 300° C.

9. A method according to claim 1, adapted to evaluate the tendency of a gasoline or an additive-containing gasoline to produce deposits on inlet valves, and wherein the temperature is kept constant at a value of 275° C.

10. A method according to claim 1, wherein adapted to evaluate the tendency of a gasoline or an additive-containing gasoline to produce deposits in combustion chambers, and wherein the temperature is kept constant at a value of 325° C. to 375°.

11. A method according to claim 1, wherein adapted to evaluate the tendency of a gasoline or an additive-containing gasoline to produce deposits in combustion chambers, and wherein the temperature is kept constant at a value of 350°.

12. A method according to claim 1, wherein said oven is part of a gas phase chromatographic system and said tube is placed in an injector placed within said oven.

* * * * *